United States Patent

Bryant, Jr. et al.

[11] Patent Number: 5,728,171
[45] Date of Patent: Mar. 17, 1998

[54] COMPOSITE/METAL PYRAMID PROSTHETIC COMPONENTS

[75] Inventors: David A. Bryant, Jr., Mt. Sterling; Eric K. Bartkus, Grove City; Robert E. Arbogast, Mt. Sterling; James M. Colvin, Hilliard, all of Ohio

[73] Assignee: Ohio Willow Wood Company, Mount Sterling, Ohio

[21] Appl. No.: 487,145

[22] Filed: Jun. 7, 1995

[51] Int. Cl.[6] .................. A61F 2/62; A61F 2/66
[52] U.S. Cl. .................. 623/38; 623/53
[58] Field of Search .................. 623/38, 53, 55, 623/47; 264/274

[56] References Cited

U.S. PATENT DOCUMENTS

| | | |
|---|---|---|
| 3,680,187 | 8/1972 | Murray .................. 264/274 X |
| 4,608,054 | 8/1986 | Schröder .................. 623/39 |
| 5,163,965 | 11/1992 | Rasmusson et al. .................. 623/36 |
| 5,376,129 | 12/1994 | Faulkner et al. .................. 623/33 |
| 5,403,179 | 4/1995 | Ramsey .................. 425/577 |
| 5,507,837 | 4/1996 | Laghi .................. 623/38 |

FOREIGN PATENT DOCUMENTS 9317640  9/1993  WIPO .................. 623/38

*Primary Examiner*—David H. Willse
*Attorney, Agent, or Firm*—Oblon, Spivak, McClelland, Maier & Neustadt, P.C.

[57] ABSTRACT

A composite and metal prosthetic component has a metal pyramid insert. The insert part includes a pyramid part and a stem having at least one slot in its bottom. Composite material may fill the spot to prevent rotation of the stem within the composite base. An annular, part spherical aluminum dome is molded onto the composite part at a position to act as a contact surface for parts mating with the pyramid part.

4 Claims, 4 Drawing Sheets

COMPOSITE/METAL PYRAMID PROSTHETIC COMPONENTS

BACKGROUND OF THE INVENTION

1. Field of the Invention

The present invention relates to prosthetic components incorporating pyramid attachments.

2. Discussion of the Background

In a prosthesis such as, but not limited to, a prosthetic leg, it is typically necessary to angularly adjust the prosthesis to the particular user's physical and ambulatory characteristics. U.S. Pat. No. 3,659,294 to Richard Glabiszewski disclosed making such adjustments by use of a joint having a metal part with a frustopyramidal boss (a "pyramid"). Set screws of a mating part abut the sides of the pyramid and angular adjustment of the joint can be performed by adjusting the set screws.

The application of the pyramid attachment method is commonly used for adjustments at the ankle, at the knee and at the attachment to the stump socket. Since stump socket adapters and knee units are still commonly made of metals, the pyramid can be easily incorporated directly into their design, eliminating the need to bolt on a separate pyramid. Therefore, the durability of knee and stump socket pyramids made entirely of metal appears to be adequate. However, for functional considerations, most foot prostheses use wood, plastic, or composites in the keel, requiring a separate "foot pyramid" to be bolted to the top of the foot. All known foot pyramids are made entirely of metal. The foot pyramid is attached to the foot with a single bolt, which can result in bolt fatigue failure when the mating surfaces of the foot pyramid and the top of the foot are not in intimate contact. In spite of this foot bolt breakage problem, which has plagued the prosthetic industry since the introduction of the foot pyramid, the pyramid attachment method has become the industry standard.

SUMMARY OF THE INVENTION

It is an object of the invention to provide a pyramid which overcomes the aforementioned shortcomings of the prior art.

It is a further object of the invention to provide a composite/metal prosthetic component having a metal pyramid insert.

The above and other objects are achieved, according to an aspect of the invention, by a metal pyramid insert for a composite and metal prosthetic component, the insert comprising a stem part having sides tapering outwardly toward a bottom to be molded into a composite base, at least one composite engaging part in said stem part, said at least one composite engaging part communicating with said tapering sides, and a pyramid part mounted to said stem part and having sides tapering outwardly toward a top thereof.

The term "composite," as used in this application, generally refers to fiber reinforced polymer resins, but is broad enough to include polymer resins without fiber reinforcement.

According to another aspect of the invention, a composite and metal prosthetic component having a metal pyramid insert comprises an insert part comprising a stem part having sides tapering outwardly toward a bottom thereof, at least one composite engaging part in said stem part, said at least one composite engaging part communicating with said tapering sides, and a pyramid part mounted to said stem part and having sides tapering outwardly toward a top thereof, and a composite part molded around said stem part with said pyramid part extending from said composite part, wherein composite material of said composite part engages said at least one composite engaging part. The composite engaging part may be a slot in the bottom of the stem part.

An annular, part spherical metal dome may be molded onto said composite part at a position surrounding said pyramid part and at a position to act as a contact surface for parts mating with said pyramid part.

Composite/metal components according to the invention offer several significant advantages over all metal counterparts, including:

1. Lighter weight. Composites can weigh substantially less than metals, so any substitution of composites for metal is beneficial with respect to weight.

2. Lower cost. Since the composite/metal components are easier to manufacture than all-metal components, the costs to produce them are lower, and their selling prices are lower.

3. Increased durability. The composites used in the composite/metal pyramid components are more flexible than metals. The flexible composite/metal pyramid components have proven to be more durable than all-metal components, especially in high impact loading, because loads are better distributed. The composite/metal pyramid components have the added advantage of improving the durability of components attached to them, also due to the better load distribution of the composite/metal components. The detrimental effects of stress concentrations on metal parts under fatigue loading is less of a problem with the composite/metal components than the all-metal components.

4. Improved safety. In addition to being more durable than all-metal components, composite/metal components give more notice of impending component failure. While a fatigued foot bolt gives little warning and fails catastrophically, composite/metal components fail in a ductile mode and give plenty of warning to the user that the metal insert may be moving.

5. Increased comfort. The flexibility of the composite/metal components increases shock absorption, making the prosthesis more comfortable for the amputee during high impact loading. The lighter weight also contributes to better comfort for the amputee.

6. Ease of use. Since molding a pyramid insert into a foot eliminates the need for a separate foot pyramid and foot bolt, assembly of the prosthesis is simplified.

The insert stem has sides which are concavely curved about a radius. The appropriate radius of the insert stem should be determined as necessary to distribute bending loads. (The stem is the portion below the inverted pyramid and is the part surrounded by composites in the molded part.)

The appropriate diameters at the top and bottom of the stem must also be determined. If the diameter at the top of the stem were too small, the insert could fail at that point. If the diameter at the top of the stem were too large relative to the bottom of the stem, little room would be left for the composite within the mold, so the insert could pull out. The diameter at the bottom of the stem is also limited by the geometry of the part in which it is molded.

The slot in the bottom of the insert prevents rotation of the metal insert within the composite. The slot allows composite material to flow in and lock the insert in place. In a small pyramid insert, a single slot across the bottom of the insert may be appropriate. In a larger pyramid insert, a double slot in an "X" pattern may be optimal. In both inserts, the slots must break through the wall of the insert stem so that air pockets cannot form, which would reduce the strength of the part.

The aluminum dome is a thin shell which acts as a wear surface for the mating component to the pyramid components. Without the aluminum dome, the composite material could deform, leading to part failure.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 3A:
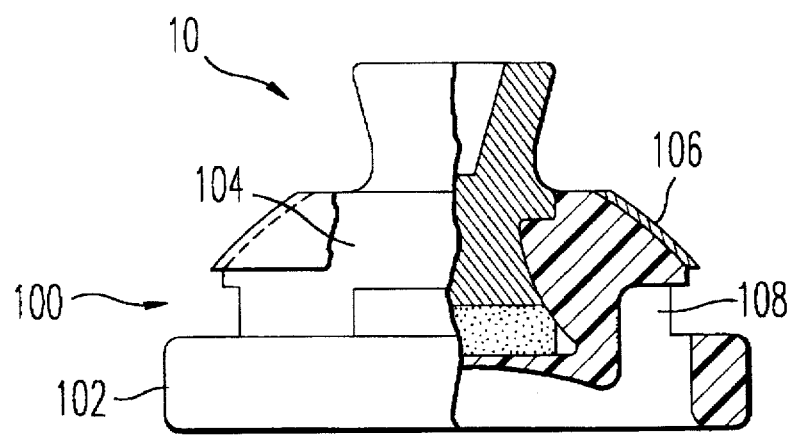
FIGS. 3A and 3B are respectively a part elevational/part sectional view of one embodiment of a composite and metal prosthetic component according to the invention, and a top view of a composite and metal prosthetic component according to the invention.
Figure 3B:
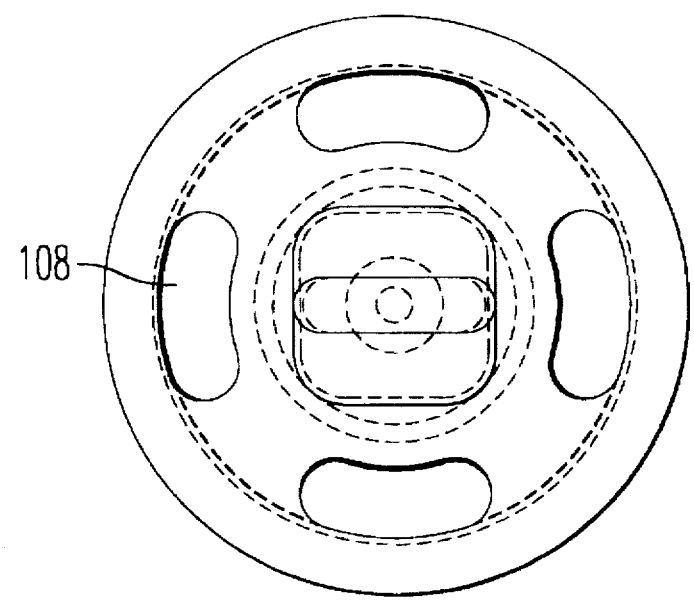

A composite and metal prosthetic component according to the invention is shown in FIGS. 3A and 3B. It includes a metal insert 10 and a composite base 100. An embodiment of the metal insert 10 is shown in FIGS. 1A–D.

The insert of FIGS. 1A–1D is preferably formed as an integral part from of a machined blank of a metal such as steel or titanium and includes a stem part 20 and a pyramid part 60. The stem part, which is to be molded into the base 100, is generally in the form of a truncated cone having concave sides with a radius R. In the illustrated embodiment, the bottom 22 of the stem part is circular and the sides 24 form a concave truncated cone tapering inwardly and then expanding, at a small radius bevel, to a generally square rim 26. The radius R should be selected to appropriately distribute the bending loads from the insert to the base 100.

Figure 1A:
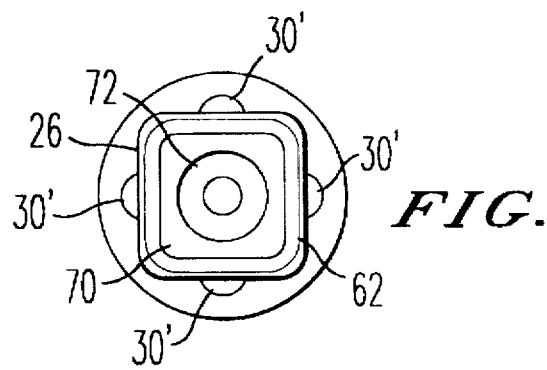
FIGS. 1A–1D are respectively top, front, side and bottom views of one embodiment of the metal pyramid insert according to the invention.
Figure 1B:
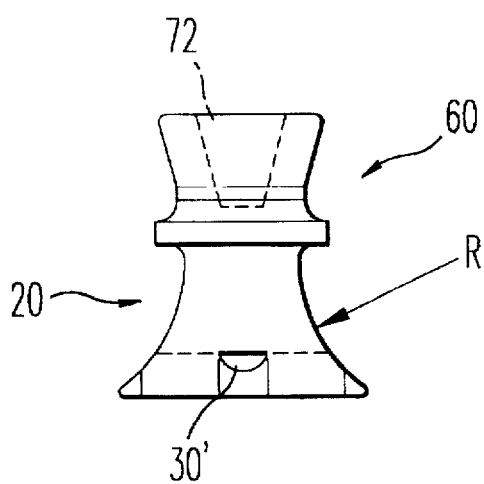
Figure 1C:
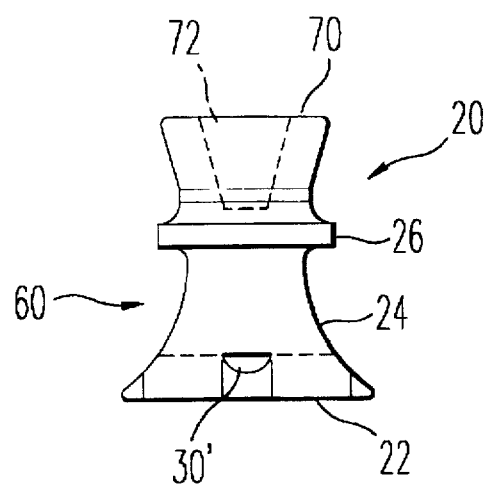
Figure 1D:
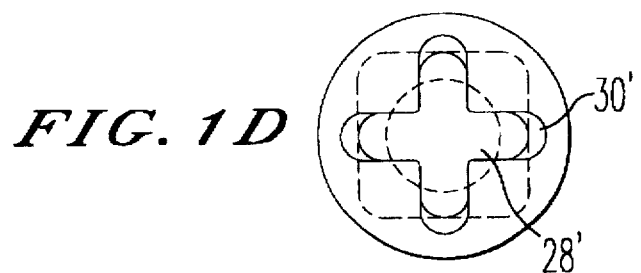
Figure 2:
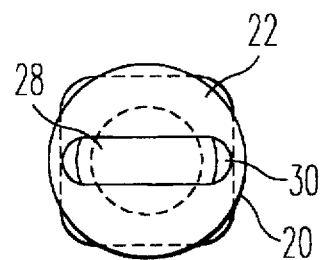
FIG. 2 corresponds to FIG. 1D but shows another embodiment of the insert bottom.

Referring to FIG. 1D, a slot 28 is formed in the bottom 22 of the stem. In FIG. 1D, the slot 28 is "X" shaped. For a smaller insert, an "I" shape may be more desirable, as shown in FIG. 2. The slot 28 should break through to the sides 24, for reasons set forth below. In the illustrated embodiment, communication between the slot and the sides 24 forms openings 30.

The pyramid part 60 of FIGS. 1A–1D extends upwardly and outwardly from the rim 26 via a small diameter bevel. It has a generally inverted frustopyramidal shape with four sides 62 which taper outwardly at a predetermined angle toward a top surface 70. A conical recess 72 extends from the top surface toward the rim in order to conserve weight. The recess should be designed so that the walls of the pyramid part 60 retain sufficient strength to support the load from the set screws of the part mating with the pyramid part.

Referring to FIGS. 3A and 3B, there is shown a composite and metal prosthetic component according to the invention, having a metal insert 10 such as that of FIGS. 1A–D molded into a composite base 100 up to the level of the top of the rim 26. The composite base has an annular lower part 102 and a generally dome shaped upper part 104. The dome shaped upper part 104 has the stem 20 of the insert 10 molded therein and has a thickness of composite material over the stem 20 sufficient to securely retain the insert 10 therein despite any bending or pulling forces applied thereto. The diameter of the top of the stem 20 should be selected to permit adequate strength for the dome part 104 while retaining adequate strength for the stem part itself. Similarly, the diameters of the top and bottom of the stem should be selected so that the taper of the stem will retain the insert 10 within the composite base.

During molding of the insert within the composite base 100, slot 28 or 28' is filled with composite material. Rotation of the insert within the base part is therefore prevented. The openings 30 or 30' prevent air pockets in the slots.

The upper portion 104 has a generally dome like surface onto which is molded an annular, part spherical aluminum dome 106 at a position surrounding the insert part. The dome 106 is a thin shell which acts as a wear surface for the mating component to the pyramid components. Without the aluminum dome, the composite material could deform, leading to part failure.

The geometry of the composite base should generally be optimized for the specific loads to be anticipated for the joint in question, and this can be done on a case by case basis.

Figure 4A:
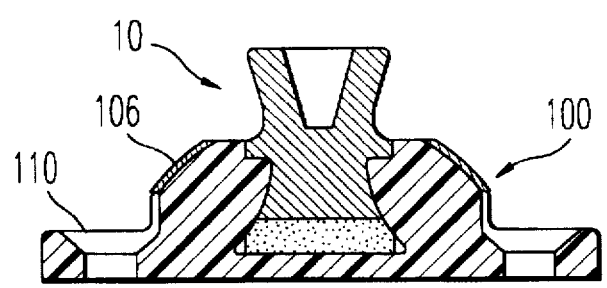
FIGS. 4A and 4B are respectively a sectional and top view of another embodiment of a composite and metal prosthetic component according to the invention.
Figure 4B:
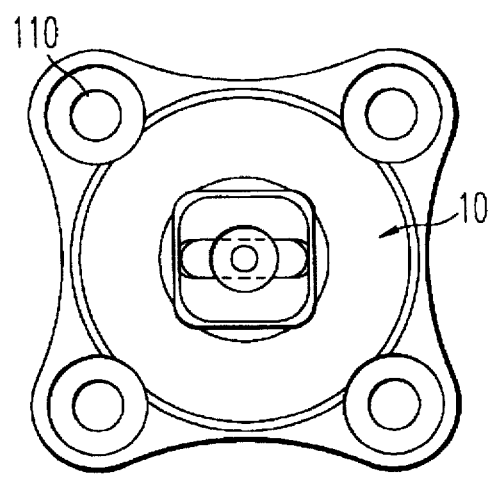
Figure 5:
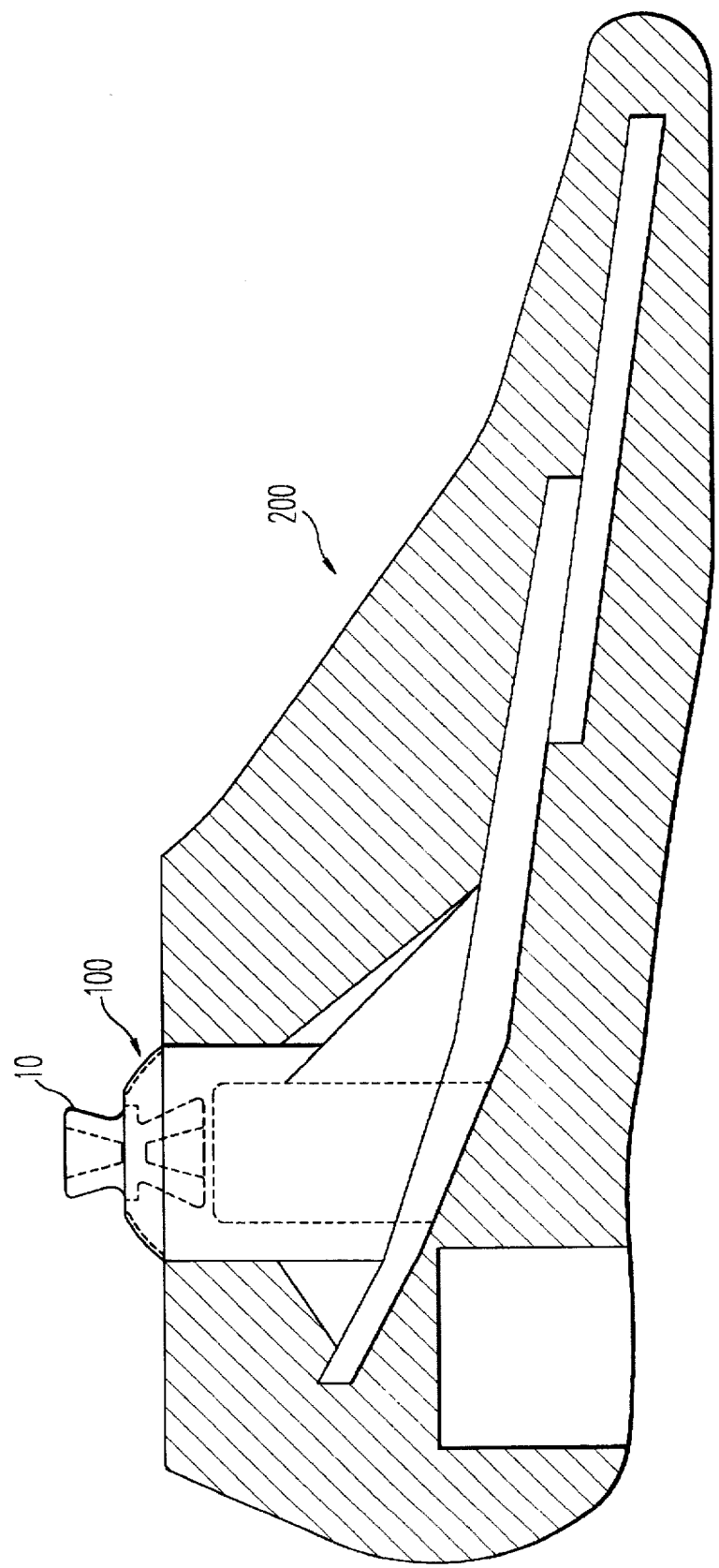
FIG. 5 illustrates an embodiment of the invention incorporated into a conventional foot.

The composite base is secured to a prosthetic part such as a prosthetic foot. For example, it may form the keel of an otherwise conventional prosthetic foot. FIG. 5 illustrates the component of the invention forming the keel of an otherwise conventional SACH foot 200. In the embodiment of FIGS. 3A and 3B, the composite base has a plurality of molded in slots 108 through which reinforcement tapes can be wound for securement of the base to the prosthetic part. The embodiment of FIGS. 4A and 4B is identical to that of FIGS. 3A and 3B except that the molded in slots are replaced by molded in mounting holes 110 for screws or bolts to be used for attaching the composite base to a prosthetic part.

Obviously, numerous modifications and variations of the present invention are possible in light of the above teachings. It is therefore to be understood that within the scope of the appended claims, the invention may be practiced otherwise than as specifically described herein.

What is claimed is:

1. A composite and metal prosthetic component, comprising:

a metal pyramid insert comprising a stem part having a top part with a smaller cross section than the bottom part, at least one composite engaging part in said stem part, and a pyramid part mounted to said stem part and having sides tapering outwardly toward a top thereof; and a composite keel of a prosthetic foot molded around said stem part with said pyramid part extending from said composite part and providing an annular, part spherical contact surface for parts mating with said pyramid part, wherein composite material of said composite keel engages said at least one composite engaging part.

2. The composite and metal prosthetic component of claim 1, wherein said annular, part spherical contact surface comprises a metal dome molded onto said composite part.

3. The composite and metal prosthetic component of claim 1, wherein said stem part has sides with a concave taper.

4. The composite and metal prosthetic component of claim 1, wherein said composite engaging part is a slot in the bottom of said stem part which communicates with the sides of said stem part.

* * * * *